(12) United States Patent
Knodel et al.

(10) Patent No.: US 9,289,208 B1
(45) Date of Patent: **\*Mar. 22, 2016**

(54) ARTICULATION INSERT FOR SURGICAL INSTRUMENT

(75) Inventors: Bryan D. Knodel, Flagstaff, AZ (US); Philipe R. Manoux, San Francisco, CA (US); Michael P. Schaller, Palo Alto, CA (US)

(73) Assignee: Cardica, Inc., Redwood City, CA (US)

( * ) Notice: Subject to any disclaimer, the term of this patent is extended or adjusted under 35 U.S.C. 154(b) by 1630 days.

This patent is subject to a terminal disclaimer.

(21) Appl. No.: 12/436,087

(22) Filed: May 5, 2009

(51) Int. Cl.
*A61B 17/072* (2006.01)

(52) U.S. Cl.
CPC .................... *A61B 17/072* (2013.01)

(58) Field of Classification Search
CPC ...................................................... A61B 17/072
USPC .................. 227/175.1, 180.1, 176.1; 606/219
See application file for complete search history.

(56) References Cited

U.S. PATENT DOCUMENTS

| | | |
|---|---|---|
| 2,515,366 A | 7/1950 | Zublin |
| 3,191,455 A | 6/1965 | Fuqua et al. |
| D210,021 S | 1/1968 | Prifogle |
| 3,497,608 A | 2/1970 | Elliott |
| 3,581,551 A | 6/1971 | Wilkinson |
| 3,583,393 A | 6/1971 | Takahashi |
| 3,650,453 A | 3/1972 | Smith, Jr. |
| 3,837,555 A | 9/1974 | Green |
| 3,899,914 A | 8/1975 | Akiyama |
| 3,986,765 A | 10/1976 | Shaffer |
| 4,086,926 A | 5/1978 | Green et al. |
| 4,127,227 A | 11/1978 | Green |
| 4,228,895 A | 10/1980 | Larkin |
| 4,328,839 A | 5/1982 | Lyons et al. |
| 4,475,679 A | 10/1984 | Fleury, Jr. |
| 4,589,416 A | 5/1986 | Green |

(Continued)

FOREIGN PATENT DOCUMENTS

| | | |
|---|---|---|
| EP | 1238634 | 9/1994 |
| JP | 2005160933 | 6/2005 |

(Continued)

OTHER PUBLICATIONS

Gong, Shao W., "Perfectly flexible mechanism and integrated mechanism system design", *Mechanism and Machine Theory* 39 (2004), (Nov. 2004),1155-1174.

(Continued)

*Primary Examiner* — Nathaniel Chukwurah
(74) *Attorney, Agent, or Firm* — Womble Carlyle Sandridge & Rice LLP

(57) ABSTRACT

An exemplary surgical apparatus may include a flexible articulation insert and at least one feeder belt extending through the articulation insert, where at least some of the staples are frangibly connected to the feeder belt. Another exemplary surgical apparatus may include at least one movable feeder belt; staples fixed to the feeder belt; and a flexible articulation insert having at least one feeder belt passage defined therein, the flexible articulation insert configured to bend through a range of motion; where each feeder belt extends through a corresponding feeder belt passage, and where each feeder belt passage is shaped such that the corresponding feeder belt and staples fixed thereto are slidable along the passage throughout the entire range of motion of the flexible articulation insert.

17 Claims, 6 Drawing Sheets

(56) References Cited

U.S. PATENT DOCUMENTS

| | | |
|---|---|---|
| 4,600,037 A | 7/1986 | Hatten |
| 4,633,861 A | 1/1987 | Chow et al. |
| 4,762,260 A | 8/1988 | Richards et al. |
| 4,869,414 A | 9/1989 | Green et al. |
| 4,969,591 A | 11/1990 | Richards et al. |
| 5,042,707 A | 8/1991 | Taheri |
| 5,143,475 A | 9/1992 | Chikama |
| 5,156,315 A | 10/1992 | Green et al. |
| 5,192,288 A | 3/1993 | Thompson et al. |
| 5,271,543 A | 12/1993 | Grant et al. |
| 5,340,330 A | 8/1994 | Dolson et al. |
| 5,381,943 A | 1/1995 | Allen et al. |
| 5,405,073 A | 4/1995 | Porter |
| 5,413,272 A | 5/1995 | Green et al. |
| 5,448,989 A | 9/1995 | Heckele |
| 5,476,206 A | 12/1995 | Green |
| 5,485,952 A | 1/1996 | Fontayne |
| 5,580,067 A | 12/1996 | Hamblin et al. |
| 5,655,698 A | 8/1997 | Yoon |
| 5,662,260 A | 9/1997 | Yoon |
| 5,673,840 A | 10/1997 | Schulze et al. |
| 5,692,668 A | 12/1997 | Schulze et al. |
| 5,704,534 A | 1/1998 | Huitema et al. |
| 5,749,828 A | 5/1998 | Solomon et al. |
| 5,772,578 A | 6/1998 | Heimberger et al. |
| 5,807,241 A | 9/1998 | Heimberger |
| 5,810,855 A | 9/1998 | Rayburn et al. |
| 5,816,471 A | 10/1998 | Plyley et al. |
| 5,823,066 A | 10/1998 | Huitema et al. |
| 5,855,311 A | 1/1999 | Hamblin et al. |
| 5,857,964 A | 1/1999 | Konstorum et al. |
| 5,894,979 A | 4/1999 | Powell |
| 5,918,791 A | 7/1999 | Sorrentino et al. |
| 5,964,774 A | 10/1999 | McKean et al. |
| 6,053,922 A | 4/2000 | Krause et al. |
| 6,306,149 B1 | 10/2001 | Meade |
| 6,364,828 B1 | 4/2002 | Yeung et al. |
| 6,391,038 B2 | 5/2002 | Vargas et al. |
| 6,431,904 B1 | 8/2002 | Berelsman |
| 6,602,252 B2 | 8/2003 | Mollenauer |
| 6,656,195 B2 | 12/2003 | Peters et al. |
| 6,716,232 B1 | 4/2004 | Vidal et al. |
| 6,755,338 B2 | 6/2004 | Hahnen et al. |
| 6,786,382 B1 | 9/2004 | Hoffman |
| 6,817,508 B1 | 11/2004 | Racenet et al. |
| 6,827,601 B1 | 12/2004 | Haeberle |
| 6,843,403 B2 | 1/2005 | Whitman |
| 7,025,747 B2 | 4/2006 | Smith |
| 7,097,089 B2 | 8/2006 | Marczyk |
| 7,140,527 B2 | 11/2006 | Ehrenfels et al. |
| 7,168,604 B2 | 1/2007 | Milliman et al. |
| 7,172,104 B2 | 2/2007 | Scirica et al. |
| 7,179,267 B2 | 2/2007 | Nolan et al. |
| 7,207,471 B2 | 4/2007 | Heinrich et al. |
| 7,213,736 B2 | 5/2007 | Wales et al. |
| 7,225,963 B2 | 6/2007 | Scirica |
| 7,225,964 B2 | 6/2007 | Mastri et al. |
| 7,234,624 B2 | 6/2007 | Gresham et al. |
| 7,238,195 B2 | 7/2007 | Viola |
| 7,300,297 B1 | 11/2007 | Wang |
| 7,316,575 B2 | 1/2008 | Muschketat |
| 7,407,077 B2 | 8/2008 | Ortiz et al. |
| 7,434,716 B2 | 10/2008 | Viola |
| 7,486,994 B2 | 2/2009 | Zarembo et al. |
| 7,506,790 B2 | 3/2009 | Shelton, IV |
| 7,507,109 B2 | 3/2009 | Tran |
| 7,575,144 B2 | 8/2009 | Ortiz et al. |
| 7,617,961 B2 | 11/2009 | Viola |
| 7,654,838 B1 | 2/2010 | Zhuge |
| 7,670,334 B2 | 3/2010 | Hueil et al. |
| 7,708,182 B2 | 5/2010 | Viola |
| 7,819,298 B2 | 10/2010 | Hall et al. |
| 8,096,457 B1 * | 1/2012 | Manoux et al. ............ 227/175.1 |
| 2003/0120284 A1 | 6/2003 | Palacios et al. |
| 2003/0236551 A1 | 12/2003 | Peterson |
| 2005/0184121 A1 | 8/2005 | Heinrich |
| 2005/0272978 A1 | 12/2005 | Brunnen et al. |
| 2006/0011699 A1 | 1/2006 | Olson et al. |
| 2006/0025811 A1 | 2/2006 | Shelton, IV |
| 2006/0041273 A1 | 2/2006 | Ortiz et al. |
| 2006/0047307 A1 | 3/2006 | Ortiz et al. |
| 2006/0151567 A1 | 7/2006 | Roy |
| 2007/0027472 A1 | 2/2007 | Hiles et al. |
| 2007/0034668 A1 | 2/2007 | Holsten et al. |
| 2007/0073341 A1 | 3/2007 | Smith et al. |
| 2007/0083234 A1 | 4/2007 | Shelton, IV et al. |
| 2007/0118163 A1 | 5/2007 | Boudreaux et al. |
| 2007/0125828 A1 | 6/2007 | Rethy et al. |
| 2007/0175947 A1 | 8/2007 | Ortiz et al. |
| 2007/0221700 A1 | 9/2007 | Ortiz et al. |
| 2007/0221701 A1 | 9/2007 | Ortiz et al. |
| 2008/0249364 A1 | 10/2008 | Korner |
| 2008/0257935 A1 | 10/2008 | Viola |
| 2009/0065552 A1 * | 3/2009 | Knodel et al. ............ 227/180.1 |
| 2009/0076506 A1 | 3/2009 | Baker |
| 2009/0090764 A1 | 4/2009 | Viola |
| 2009/0177041 A1 | 7/2009 | Stefanchik et al. |

FOREIGN PATENT DOCUMENTS

| | | |
|---|---|---|
| RU | 2080833 | 6/1997 |
| WO | WO-81/01953 | 7/1981 |
| WO | WO-85/01427 | 4/1985 |
| WO | WO2004/103430 | 12/2004 |

OTHER PUBLICATIONS

Lim, Jonas J., et al., "A review of mechanism used in laparascopic surgical instruments", *Mechanism and Machine Theory* 38, (2003),1133-1147.

Lim, Jyue B., "Type Synthesis of a Complex Surgical Device", *Masters Thesis*, (Feb. 21, 2001).

Lim, Jonas J., et al., "Application of Type Synthesis Theory to the Redesign of a Complex Surgical Instrument", *Journal of Biomechanical Engineering* (124), (Jun. 2004),265-272.

Kolios, Efrossini et al., "Microlaparoscopy", *J. Endourology* 18(9), (Nov. 2004),811-817.

Steichen, Felicien M., et al., "Mechanical Sutures in Surgery", *Brit. J. Surg* 60(3), (Mar. 1973),191-197.

"Cardica Microcutter Implant Delivery Device 510(k), Cover Sheet, Table 10.1, "Substantial Equivalence Comparison," and Section 12, "Substantial Equivalence Discussion"",

* cited by examiner

ARTICULATION INSERT FOR SURGICAL INSTRUMENT

FIELD OF THE INVENTION

The invention generally relates to an articulated surgical instrument, and more specifically to an articulated surgical stapler.

BACKGROUND

Minimally invasive surgery is performed through small incisions in the body, into which trocar ports may or may not be placed. One or more surgical instruments are inserted through each incision in order to perform the surgical procedure. In order to effectuate one of the objectives of minimally invasive surgery, which is the minimization of incisions to the body to reduce healing time and scarring, it is desirable to minimize the number of incisions made in the body. The number of incisions and their placement are determined by the particular surgical procedure to be performed and the configuration of the instruments used to carry out that procedure.

One problem encountering during the performance of a minimally invasive surgical procedure is access to the tissue to be treated. Depending on the specific anatomy of the patient, it may be difficult to reach an area to be treated with a specific surgical instrument. As a result, one or more additional incisions may need to be made in the patient in order to access that tissue. Or, the surgeon may need to obtain a different surgical instrument, adding to the time and expense of the procedure. Additionally, where more incisions may be made or additional instruments may be utilized, it can be difficult and/or time-consuming for the surgeon to find the surgical site again.

BRIEF DESCRIPTION OF THE DRAWINGS

The use of the same reference symbols in different figures indicates similar or identical items.

DETAILED DESCRIPTION

U.S. patent application Ser. No. 11/851,379, filed Sep. 6, 2007; U.S. patent application Ser. No. 11/956,988, filed Dec. 14, 2007; U.S. patent application Ser. No. 12/263,171, filed Oct. 31, 2008; and U.S. patent application Ser. No. 12/436, 014, filed May 5, 2009 (the "Endocutter Documents") are hereby incorporated by reference herein in their entirety. U.S. patent application Ser. No. 12/400,760, filed Mar. 9, 2009 (the "Articulation Document") is also hereby incorporated by reference herein in its entirety.

Surgical Instrument

Figure 1:
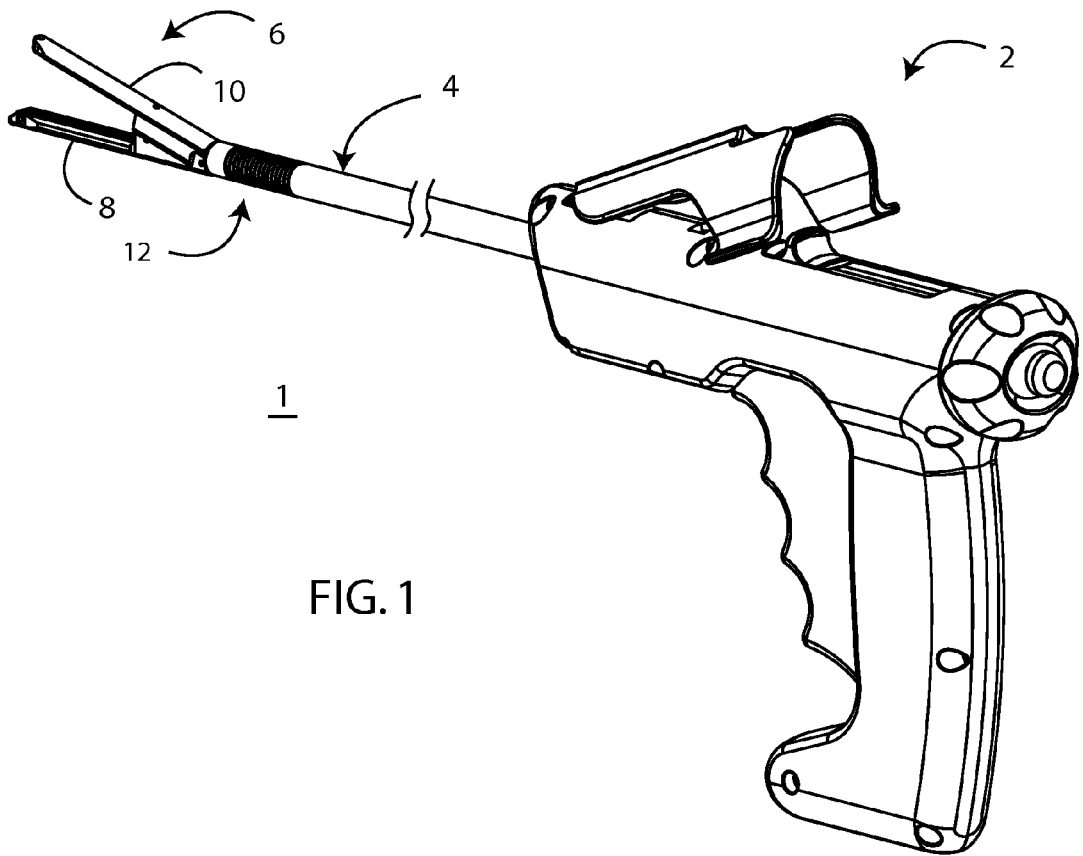
FIG. 1 is a perspective view of a an exemplary surgical instrument.

Referring to FIG. 1, a surgical instrument 1 includes a handle 2 attached to a shaft 4, which in turn is attached to an end effector 6. The surgical instrument 1 may be an endocutter, a linear cutter, a stapler, or any other suitable surgical instrument. The end effector 6 may be one or more separate components that are connected to the shaft 4, or may be fabricated integrally with the distal end of the shaft 4. As discussed in greater detail below, the end effector 6 may be fixed to the shaft 4, or may be separable from the shaft 4 such that a fresh end effector 6 may be attached to the shaft 4 after one or more actuations of the surgical instrument. The end effector 4 and at least the distal end of the shaft 4 may be sized to pass through an incision or through a standard trocar port that may be placed in the patient. Advantageously, the end effector 4 may be sized to pass through a trocar port, having an opening between 5-10 millimeters in diameter. Alternately, the surgical instrument 1 may be used in the course of conventional open surgery, where a trocar port is not used. The end effector 4 may include a staple holder 8 connected to an anvil 10, and may be movable between an open configuration and a closed configuration. In the closed configuration, tissue may be clamped between the staple holder 8 and the anvil 10. Alternately, the end effector 4 may omit the anvil 10. Alternately, the end effector 4 need not include a staple holder 8 or anvil 10, and the end effector 4 may instead be a different surgical instrument, such as but not limited to a bipolar cutter, a biopsy device, a grasper, or a stabilizer.

Figure 2:
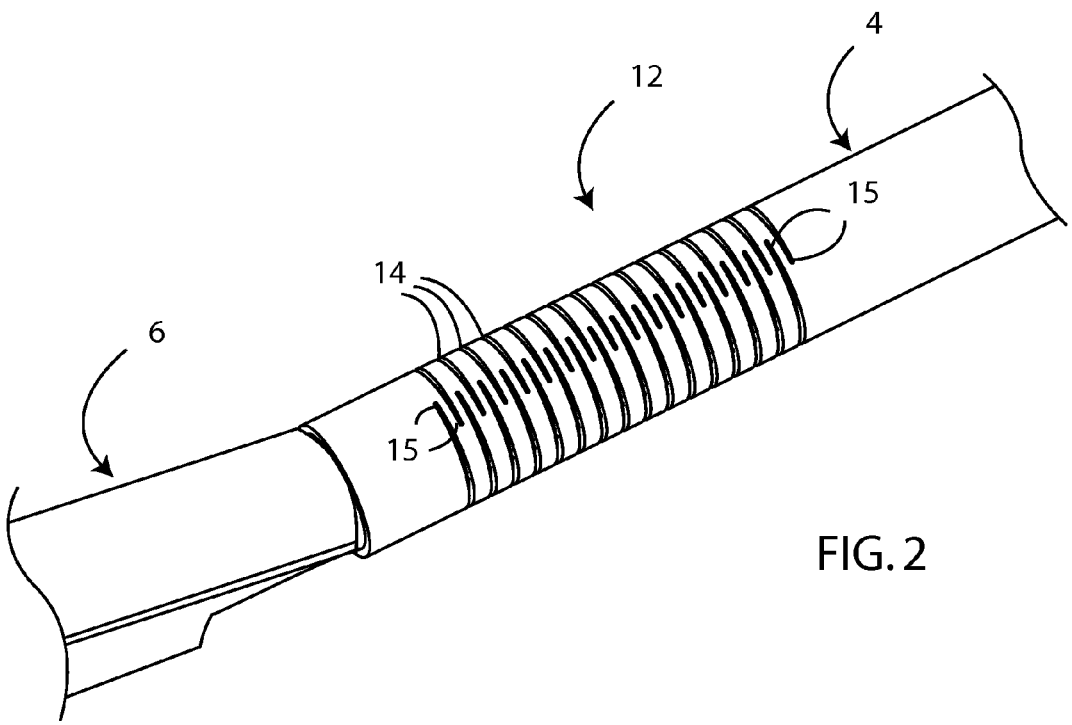
FIG. 2 is a detail perspective view of an exemplary articulated region on a shaft of the surgical instrument of FIG. 1.

The shaft 4 advantageously has a tubular shape with a lumen defined therein. Optionally, the shaft 4 may include a cutaway, trough or other feature (not shown) to allow a guidewire (if any) or other positioning aid that may be used in the surgical procedure to remain in place during actuation of the surgical instrument 1. The shaft 4 may be flexible or rigid, in whole or in part. The shaft 4 may be articulated in at least one location, if desired. Referring to FIG. 2, as one example, the shaft 4 may be generally rigid, with the exception of a flexible articulated region 12 that connects two generally-rigid segments of the shaft 4. The articulated region 12 may be configured and operated substantially as set forth in the Articulation Document. As an example of an articulated region 12, a plurality of slots 14 may be located in the shaft 4 in the articulated region 12. The slots 14 may extend completely through the wall of the shaft 4 from the outer surface of the shaft to the lumen in the shaft 4. The slots 14 may be arranged in any suitable manner. As one example, each slot 14 may extend along greater than 180 degrees of circumference of the shaft 4, between two vertices 15. Proceeding proximally along the shaft 4, at least two slots 14 may be generally arranged in an alternating manner. That is, one slot 14 may open generally in one direction away from the longitudinal centerline of the shaft 4, and the slot 14 proximal to that may open generally in the opposite direction away from the longitudinal centerline of the shaft 4. To accomplish this, the vertices 15 of a slot opening (for example) laterally to the left may be located laterally to the right of the vertices of a longitudinally adjacent slot opening laterally to the right. As a result, where at least two slots 14 extend along greater than 180 degrees of circumference of the shaft 4, no line on the surface of the shaft 4 that is parallel to the longitudinal centerline of the shaft 4 can extend completely through the articulating region 12 without encountering a slot 14. Put another way, every line on the surface of the shaft 4 that is parallel to the longitudinal centerline of the shaft 4 crosses at least slot 14. The slots 14 may be oriented and arranged relative to one another to provide for lateral articulation of the shaft 4. That is, the slots 14 may be oriented and arranged such that the portion of the shaft 6 distal to the articulating region 12 is rotatable in a single plane, laterally left and right. Alternately, the slots 14 may be oriented and arranged such that the portion of the shaft 6 distal to the articulating region 12 is rotatable in a single plane in a direction other than laterally left and right. Alternately, the slots 14 may be oriented and arranged such that the portion of the shaft 6 distal to the articulating region 12 is rotatable in more than a single plane.

Figure 3:
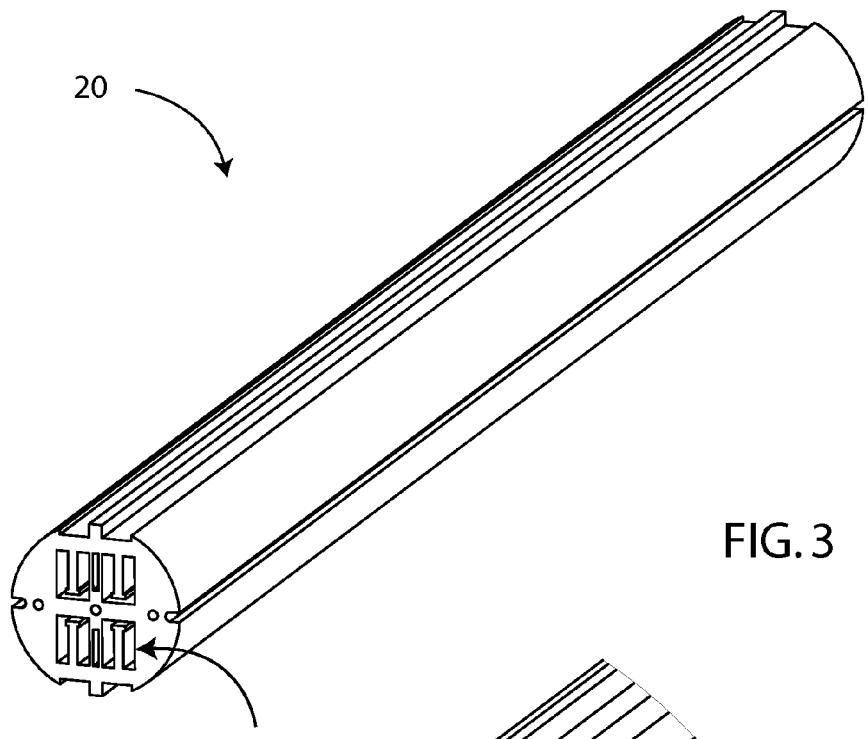
FIG. 3 is a perspective view of an exemplary articulation insert.
Figure 4:
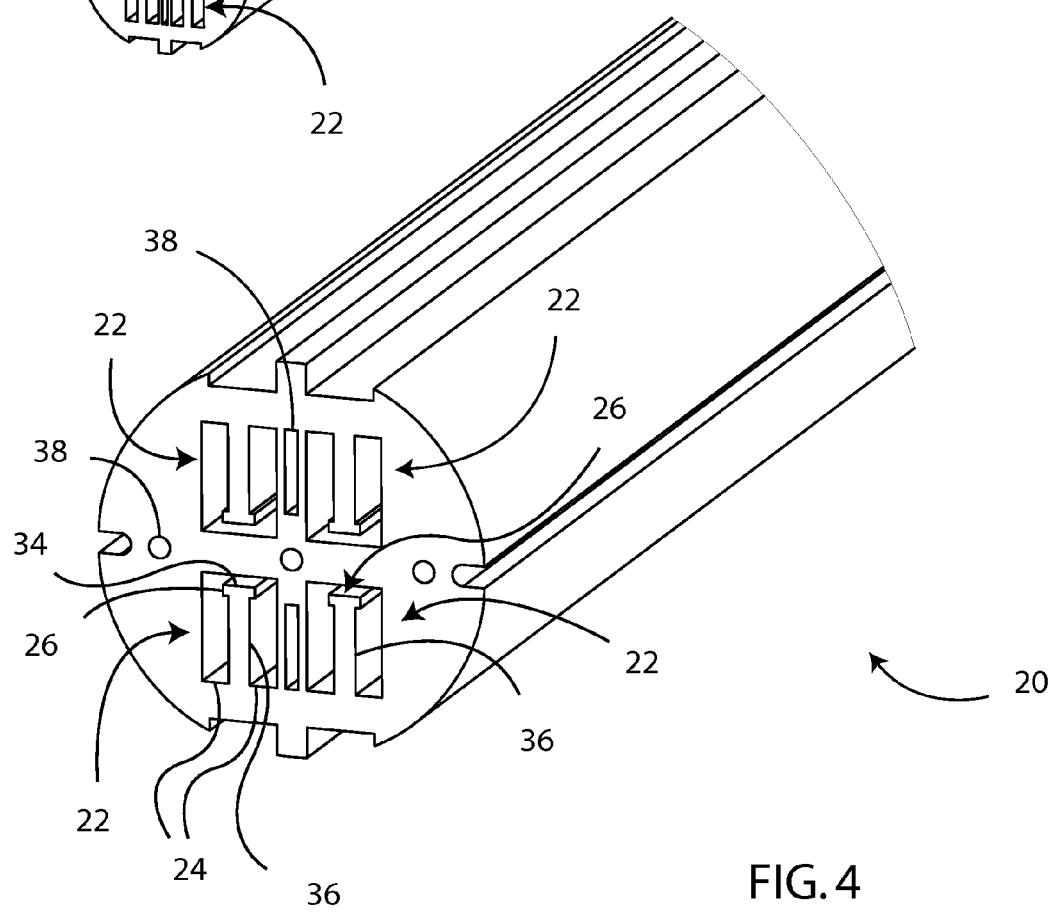
FIG. 4 is a detail end view of the articulation insert of FIG. 3.

Referring also to FIGS. 3-4, one example of an articulation insert 20 is shown. The articulation insert 20 is placed inside the lumen of the shaft 4, such that at least part of the articulation insert 20 is located in the articulating region 12 of the shaft 4. The articulation insert 20 may be fixed to the shaft 4 along part or all of its length. Alternately, the articulation insert 20 may be movable relative to the lumen of the shaft 4 along at least part of its length. The articulation insert 20 of FIG. 3 is a flexible, unitary solid, fabricated from any suitable material. As one example, at least part of the articulation insert 20 may be fabricated from or coated with polytetrafluoroethylene (PTFE). Alternately, at least part of the articulation insert 20 may be coated with any lubricious material, such as, for example, sodium stearate. Alternately, the articulation insert of FIG. 3 may have two or more separate, independent sections. At least one passage 22 is defined longitudinally through the articulation insert 20. The passages 22 may be arranged such that the articulation insert 20 is bilaterally symmetrical about two different perpendicular planes. In this way, at least part of the articulation insert 20 is bendable in a direction away from the longitudinal axis of the articulation insert 20 in the straight configuration shown in FIG. 1, without a preferred bending direction of the articulation insert 20 being established. In such a configuration, at least one of the passages 22 may be empty. Alternately, the articulation insert 20 may be bilaterally symmetrical about only a single plane, or may be asymmetrical.

Figure 4A:
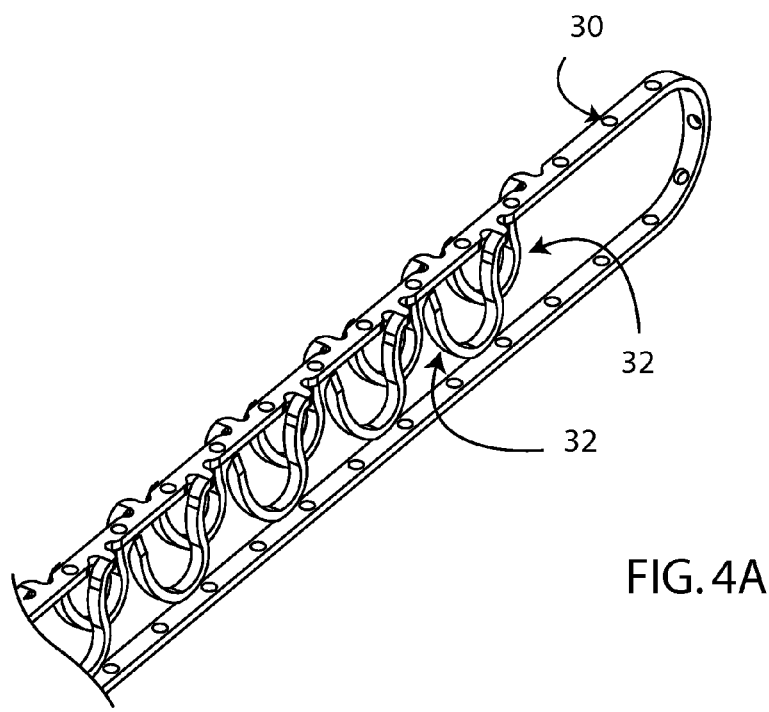
Figure 5:
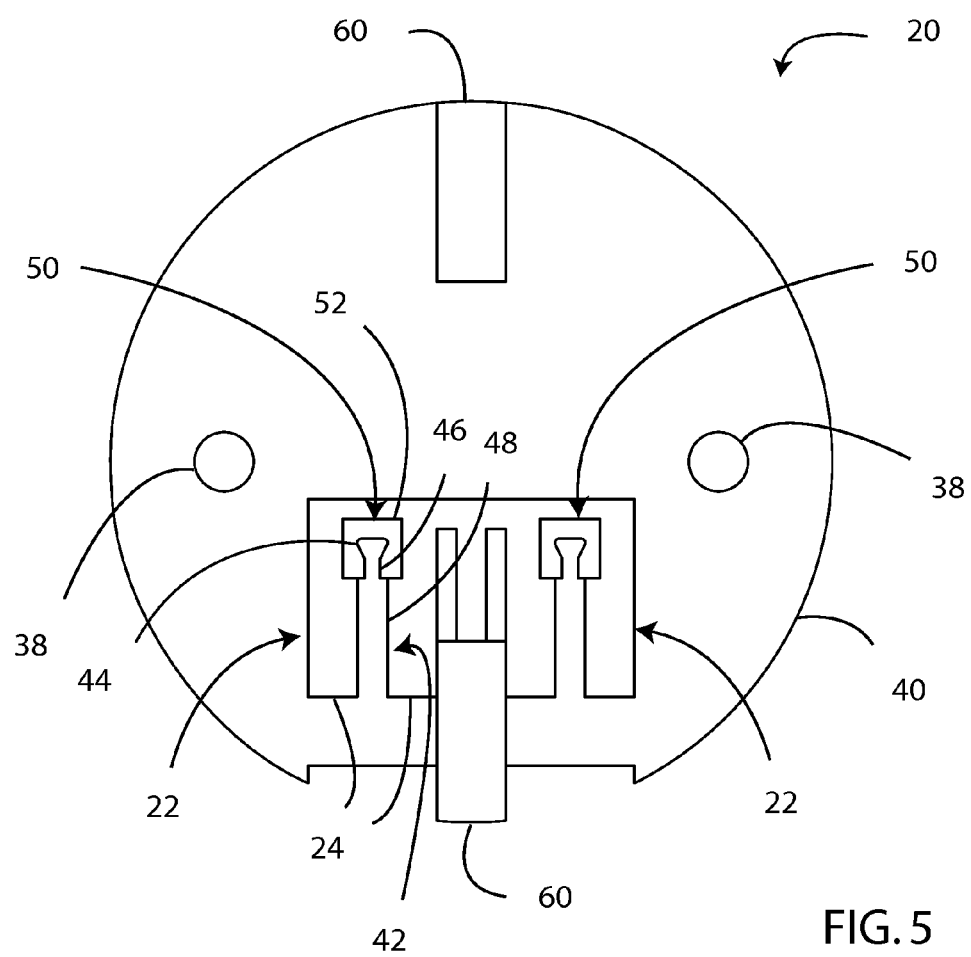
FIG. 5 is an end view of another exemplary articulation insert.

Each passage 22 may have any suitable cross-sectional shape. The cross-sectional shape of each passage 22 may be substantially constant along its length, or may vary along at least part of its length. Two or more passages 22 may connect with one another at one or more points along their length. Referring also to FIG. 4A, at least one of the passages 22 is sized and shaped to receive a feeder belt 30 therethrough, where staples 32 are frangibly connected to that feeder belt 30. The feeder belt 30 and staples 32 may be substantially as described in the Endocutter Documents. At least one passage 22 may include two staple passages 24 in which the staples 32 of the feeder belt 30 are received, separated by a generally T-shaped platform 26. The top 34 of the T-shaped platform 26 is narrow enough to receive the corresponding feeder belt 30 on its surface, such that the feeder belt 30 is slidable along the top 34 of the T-shaped platform. The top 34 of the T-shaped platform 26 is also wider than the column 36 underneath, which may be undercut relative to the top 34 of the T-shaped platform 26. The narrower column 36 allows the staples 32 room to move as the articulation insert 20 bends, as described in greater detail below. Alternately, the T-shaped platform 26 may have any other suitable shape. As one example, it may be V-shaped, where the wider end of the V is the top 34 on which a feeder belt 30 slides. One or more additional passages 38 may be provided through the articulation insert 20, such that a control member or other structure or mechanism can pass from the handle 2 along the shaft 4 through the passage or passages 38 to the end effector 6.

Referring to FIGS. 5-10, another example of an articulation insert 20 is shown. The articulation insert 20 is placed inside the lumen of the shaft 4, such that at least part of the articulation insert 20 is located in the articulating region 12 of the shaft 4. The articulation insert 20 may be fixed to the shaft 4 along part or all of its length. Alternately, the articulation insert 20 may be movable relative to the lumen of the shaft 4 along at least part of its length. The articulation insert 20 of FIGS. 5-10 is fabricated from multiple individual inserts 40 flexibly connected together, and may be referred to as the accordion configuration. Each individual insert 40 may be a thin, generally circular plate. Alternately, one or more individual inserts 40 may have a different shape, thickness or configuration. Advantageously, the inserts 40 are rigid. Alternately, at least one insert 40 is at least partly flexible.

Advantageously, the individual inserts 40 include cutouts defined therein that collectively define passages 22 of similar shape and size as the cross-section of the flexible solid of FIGS. 3-4, such that the shape of the cutouts are substantially the same as set forth above with regard to FIGS. 3-4. At least one passage 22 may include two staple passages 24 in which the staples 32 of the feeder belt 30 are received, separated by a wall 42. The wall 42 may include a wide area 44 at its top, narrowing generally angularly to a narrow strut 46 that connects to a wider, lower portion 48 of the wall 42. A rail 50 may extend between the individual inserts 40, connected to the upper portion of each wall 42. The rail 50 may include a cavity having substantially the opposite shape of the wide area 44 and the strut 46 of the wall 42, such that the rail 50 is held securely on top of the wall 42. Advantageously, each rail 50 is slidable in the direction perpendicular to the page with regard to FIG. 5 relative to the corresponding wall 42, as described in greater detail below. Alternately, at least one rail 50 may be fixed to at least one wall 42. The top 52 of the rail 50 is narrow enough to receive the corresponding feeder belt 30 on its surface, such that the feeder belt 30 is slidable along the top 52 of the rail 50. The top 52 of the rail 50 is also wider than the wall 42 underneath, which allows the staples 32 room to move as the articulation insert 20 bends, as described in greater detail below. The combination of the rail 50 and the wall 42 is generally T-shaped in cross-section.

At least one flexible beam 60 may be fixed to each of the individual inserts 40. The beam or beams 60 may thus provide spacing between the individual inserts 40 and hold them in a desired orientation. Alternately, at least one beam 60 is not fixed relative to at least one individual insert 40, such that relative motion therebetween is allowed. The beam or beams 60 may be fabricated from any suitable material. Optionally, successive individual inserts 40 may be separated by O-rings (not shown) or other cushioning material. If so, the O-rings or other cushioning material are either located outside of the passages 22, or include apertures or passages therein aligned with the passages 22 to allow each feeder belt 30 to move through the corresponding passage without interference.

Figure 6:
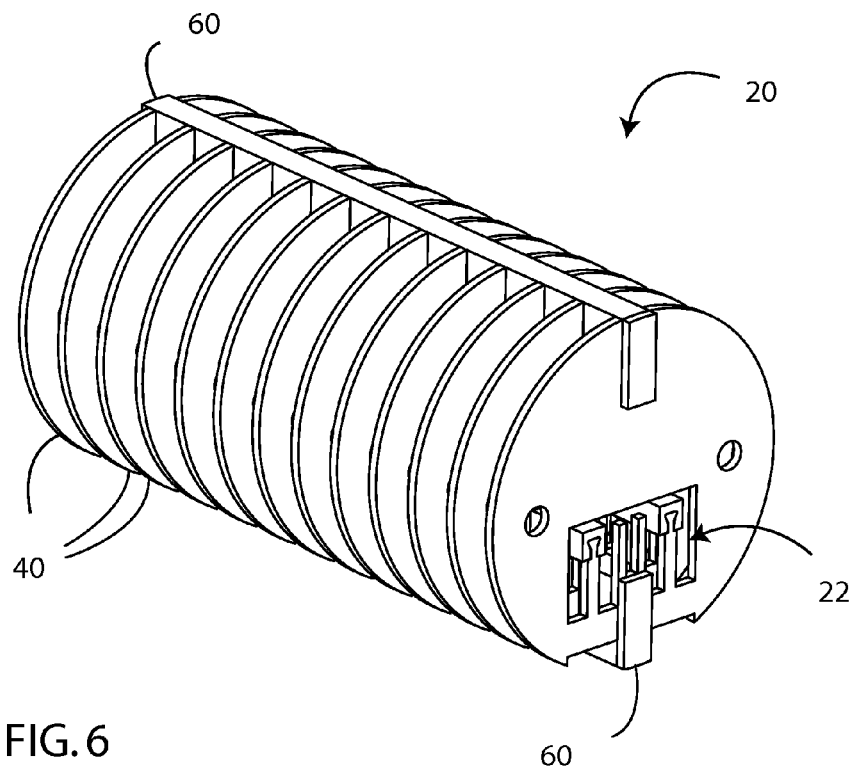
FIG. 6 is a perspective view of the articulation insert of FIG. 5 in a straight configuration.
Figure 7:
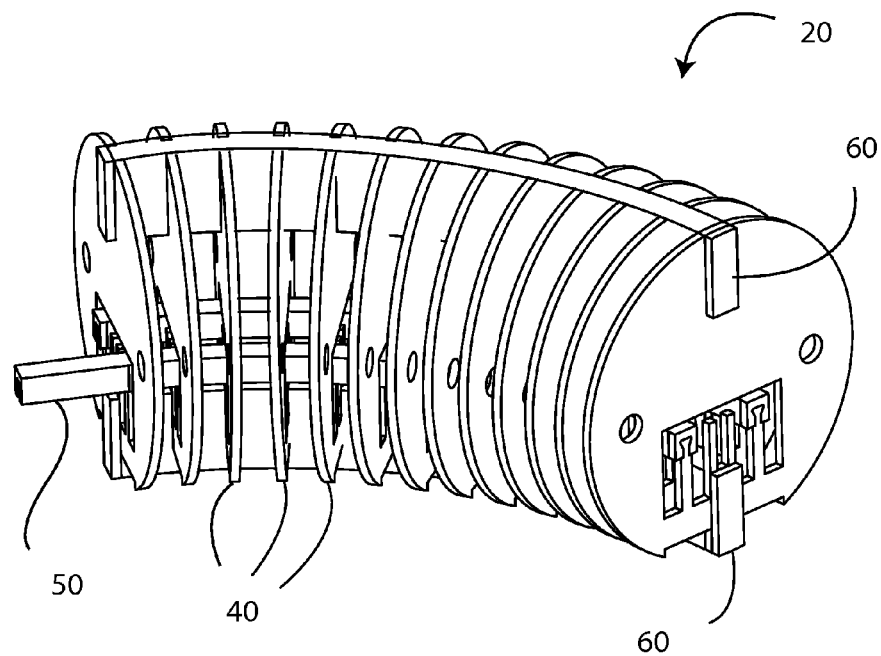
FIG. 7 is a perspective view of the articulation insert of FIG. 5 in a curved configuration.
Figure 8:
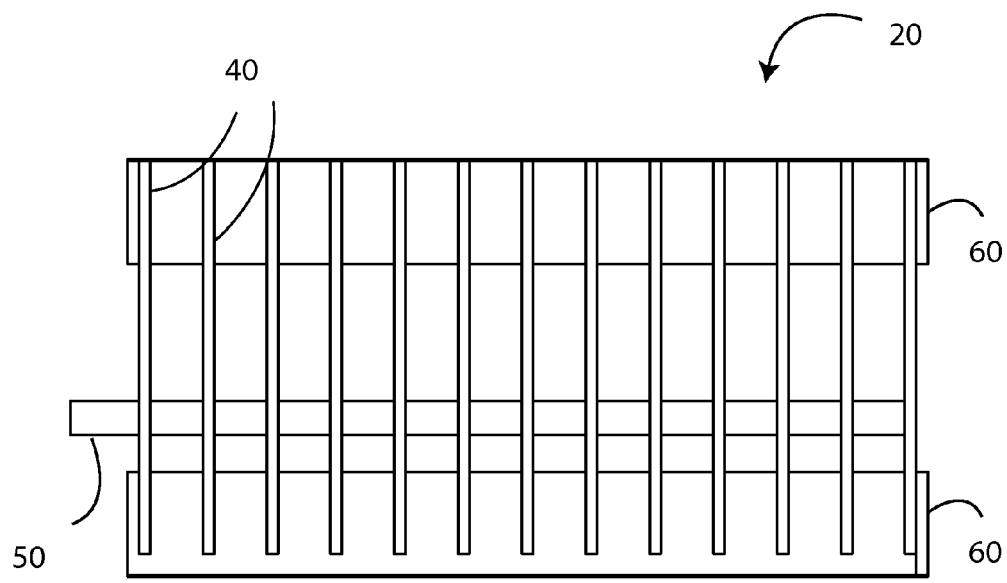
FIG. 8 is a side view of the articulation insert of FIG. 5 in a straight configuration.
Figure 9:
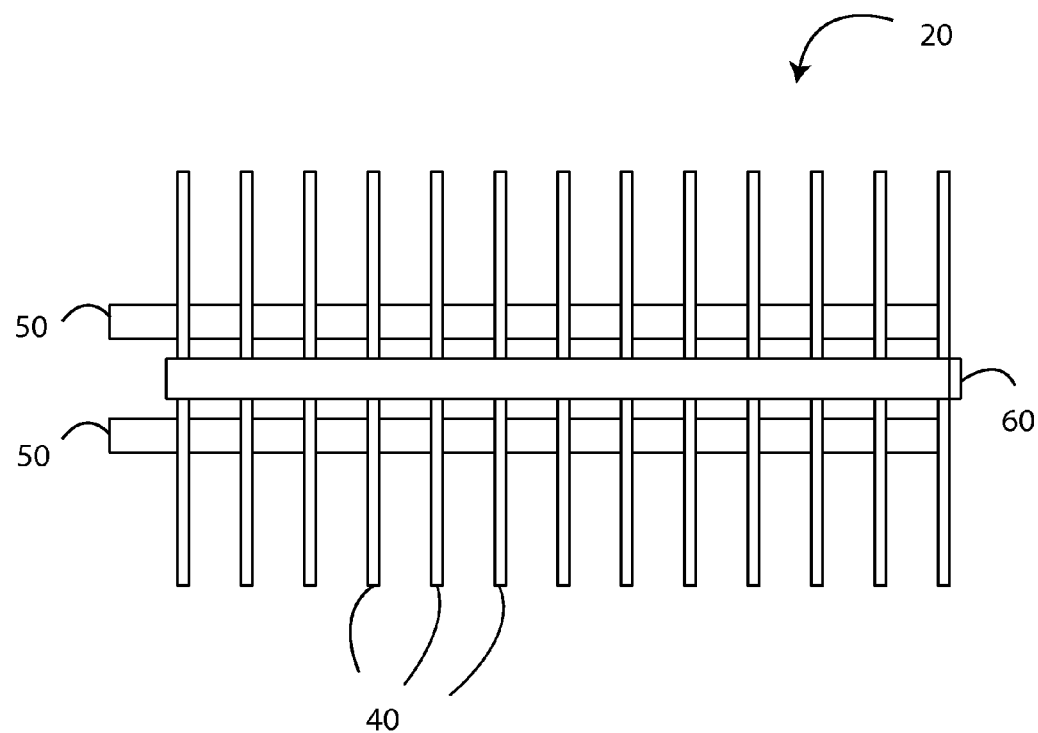
FIG. 9 is a top view of the articulation insert of FIG. 5 in a straight configuration.

Referring to FIG. 6, the articulation insert 20 is in a configuration in which its longitudinal centerline is substantially straight. This configuration is advantageously the neutral state of the articulation insert 20, which is the configuration assumed by the articulation insert 20 when no external forces are acting upon it. In the neutral state, the individual inserts 40 may be substantially parallel to one another, and the beam or beams 60 and rail or rails 50 may be substantially perpendicular to the individual inserts 40. Alternately, at least one individual insert 40 may be configured or oriented differently in the neutral state, and/or at least one beam 60 or rail 50 may be configured or oriented differently in the neutral state. Alternately, the articulation insert 20 may be in its neutral state when it is curved such as shown in FIG. 7. Referring to FIG. 8, at least one rail 50 may be longer than the remainder of the articulation insert 20 in the neutral state, such that the distal end of that rail 50 extends distal to the most-distal individual insert 40, the proximal end of that rail 50 extends proximal to the most-proximal individual insert 40, or both. Optionally, one rail 50 extends distal to a remainder of the articulation insert 20, and the other rail 50 extends proximal to a remainder of the articulation insert 20.

Operation

The end effector 6 of the surgical instrument 1 is introduced into the body of the patient such as described in the Endocutter Documents and the Articulation Document. The end effector 6 may be articulated such as described in the Articulation Document, before and/or after introduction of the end effector 6 into the patient. Bending of the shaft 4 is focused in and substantially restricted to the articulated region 12. As a consequence of bending of the articulated region 12, the articulation insert 20 is bent as well. Alternately, articulation may be caused by manipulating the articulation insert 20 to in turn cause bending of the articulated region 12 of the shaft 4. The articulated region 12 may be configured to bend through a known range of motion.

Figure 10:
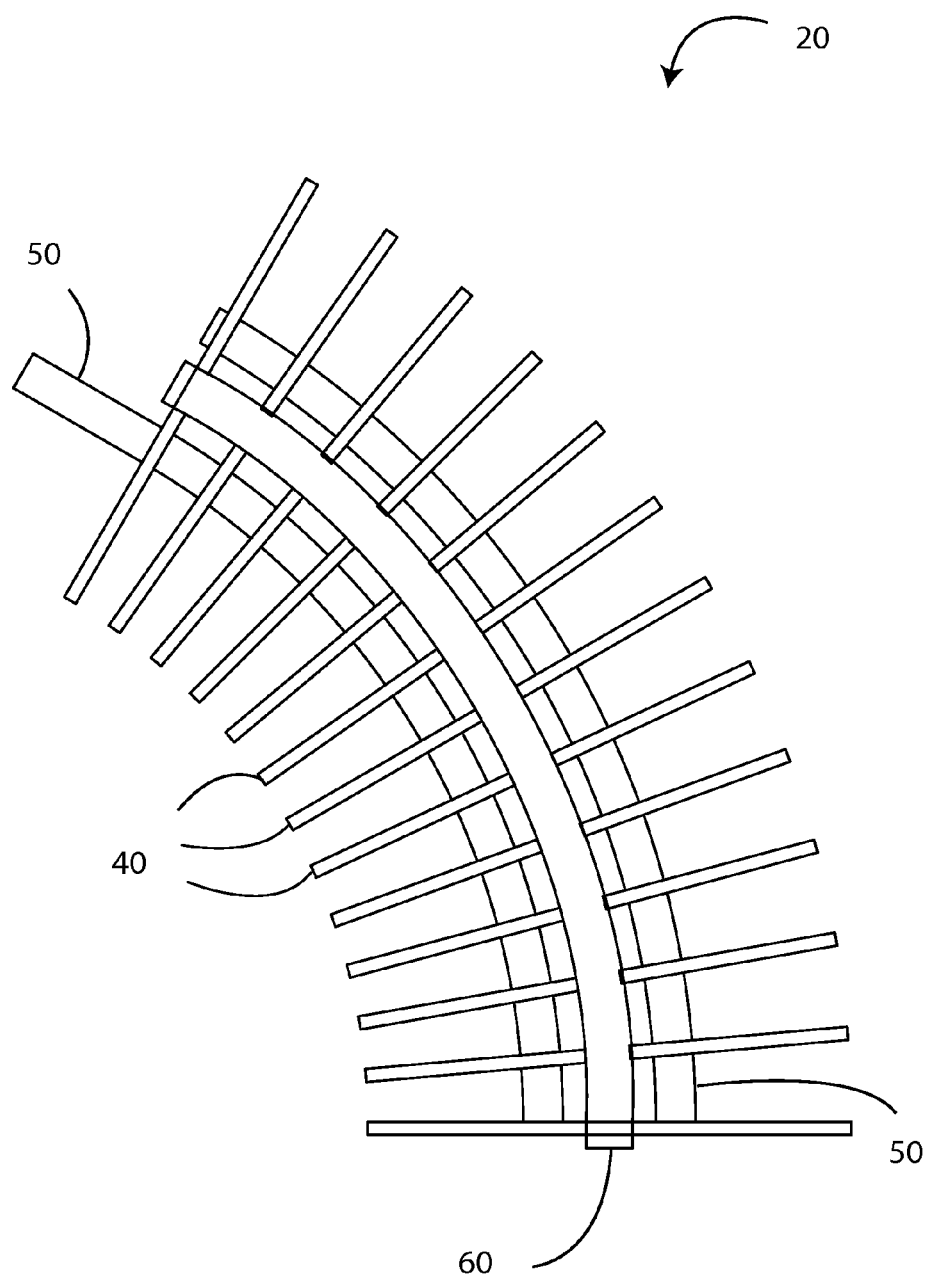
FIG. 10 is a top view of the articulation insert of FIG. 5 in a curved configuration.

As the articulated region 12 bends, the articulation insert 20 bends. Where the articulation insert 20 has the accordion configuration of FIGS. 5-10, the rails 50 advantageously slide relative to the corresponding walls 42 of the passages 22. In this way, the upper surface 52 of each rail 50 remains substantially flat, because the rails 50 are not compressed or expanded as the articulation insert 20 bends, but rather are free to slide relative to the individual inserts 40. As seen in FIGS. 7 and 10, bending of the articulation insert 20 may cause at least one end of at least one rail to slide outward from a remainder of the articulation insert. As the articulated region 12 bends, where the articulation insert 20 is a flexible solid, the free ends of the staples 32 in a passage 22 on one side of each T-shaped platform 26 move under the top 34 of that T-shaped platform 26 into the space provided by the narrower column 36, substantially without interfering with the T-shaped platform 26. As the articulated region 12 bends, where the articulation insert 20 has an accordion configuration, the free ends of the staples 32 in a passage on one side of each wall 42 move under the rail 50 into the space provided by the narrow wall 42 as compared to the rail 50, substantially without interfering with the wall 42. Thus, each exemplary articulation insert 20 facilitates bending of the feeder belt 30 without prematurely bending the staples 32.

Where O-rings or other cushioning material is provided between successive individual inserts 40 of the articulation insert 40, the bending of the articulated insert 40 compresses a portion of each O-ring or other material between successive individual inserts 40. In this way, separation between those successive individual inserts 40 may be more easily maintained.

The surgical instrument 1 may then actuate the end effector 6 such as set forth in the Endocutter Documents and the Articulation Document. If the surgeon desires to use the end effector 6 at a different location within the patient, and the surgical instrument 1 includes one or more feeder belts, as described in the Endocutter Documents, the feeder belt or belts 30 may be advanced, placing a fresh set of staples in position for deployment within the staple holder. Such advancement may be accomplished as set forth in the Endocutter Documents. Where the articulation insert 20 is a flexible solid, each feeder belt 30 slides along the top 34 of the corresponding T-shaped platform 26. Optionally, the top 34 may be lubricated with any lubricious material or coating, such as PTFE, or the T-shaped platform 26 may be fabricated from a lubricious material. The width of the top 34 of the T-shaped platform 26 as compared to the column 36 prevents the staples 32 from colliding with the column 36, such that the feeder belt 30 can advance. The narrowness of the column 36 advantageously is selected based on the range of motion of the articulated region 12, such that the feeder belt or belts 30 can be advanced regardless of the degree of articulation of the end effector 6. Alternately, the end effector 6 must first be moved to a lesser degree of articulation before advancing the feeder belt or belts 30. Where the articulation insert has an accordion configuration, each feeder belt 30 slides along the top 52 of the corresponding rail 50. Optionally, the top 52 may be lubricated with any lubricious material or coating, such as PTFE, or the rail 50 may be fabricated from a lubricious material. The width of the rail 50 as compared to the wall 48 prevents the staples 32 from colliding with the wall 48, such that the feeder belt 30 can advance. The narrowness of the wall 48 advantageously is selected based on the range of motion of the articulated region 12, such that the feeder belt or belts 30 can be advanced regardless of the degree of articulation of the end effector 6. Alternately, the end effector 6 must first be moved to a lesser degree of articulation before advancing the feeder belt or belts 30.

While the invention has been described in detail, it will be apparent to one skilled in the art that various changes and modifications can be made and equivalents employed, without departing from the present invention. It is to be understood that the invention is not limited to the details of construction, the arrangements of components, and/or the method set forth in the above description or illustrated in the drawings. For example, the articulation insert 20 may be used to pass mechanisms and/or structures through an articulating region 12 of a shaft 4 other than a feeder belt 30 and/or staples 32. Statements in the abstract of this document, and any summary statements in this document, are merely exemplary; they are not, and cannot be interpreted as, limiting the scope of the claims. Further, the figures are merely exemplary and not limiting. Topical headings and subheadings are for the convenience of the reader only. They should not and cannot be construed to have any substantive significance, meaning or interpretation, and should not and cannot be deemed to indicate that all of the information relating to any particular topic is to be found under or limited to any particular heading or subheading. Therefore, the invention is not to be restricted or limited except in accordance with the following claims and their legal equivalents.

What is claimed is:

1. Surgical apparatus, comprising:
   a flexible articulation insert; and
   at least one feeder belt extending through said articulation insert, wherein a plurality of staples are frangibly affixed to said feeder belt.

2. The surgical apparatus of claim 1, incorporating by reference all of the elements of that claim; further comprising a shaft with a lumen therein and an articulated region; wherein at least part of said articulation insert is positioned within the lumen of the shaft at said articulation.

3. The surgical apparatus of claim 1, incorporating by reference all of the elements of that claim; wherein said articulation insert is a flexible solid having at least one passage defined longitudinally therethrough.

4. The surgical apparatus of claim 3, incorporating by reference all of the elements of that claim; wherein at least one said passage includes two spaced-apart staple passages separated by a generally T-shaped platform.

5. The surgical apparatus of claim 3, incorporating by reference all of the elements of that claim; wherein said articulation insert is substantially bilaterally symmetrical.

6. The surgical apparatus of claim 3, incorporating by reference all of the elements of that claim; further comprising an end effector connected to said shaft and at least one control member extending from said end effector through said lumen of said shaft, wherein at least one said passage receives a corresponding said feeder belt and at least one other said passage receives at least one said control member.

7. The surgical apparatus of claim 3, incorporating by reference all of the elements of that claim; wherein said articulation insert is at least partially composed of PTFE.

8. The surgical apparatus of claim 1, incorporating by reference all of the elements of that claim; wherein said articulation insert comprises a plurality of individual inserts flexibly connected to one another.

9. The surgical apparatus of claim 8, incorporating by reference all of the elements of that claim; wherein at least one said individual insert is a plate.

10. The surgical apparatus of claim 8, incorporating by reference all of the elements of that claim; wherein at least one said individual insert is rigid.

11. The surgical apparatus of claim 8, incorporating by reference all of the elements of that claim; wherein said articulation insert has a neutral state, and wherein said individual inserts are generally parallel to one another in said neutral state.

12. The surgical apparatus of claim 8, incorporating by reference all of the elements of that claim; further comprising at least one beam fixed to each said individual insert.

13. The surgical apparatus of claim 8, incorporating by reference all of the elements of that claim; wherein each said individual insert includes at least one aperture defined therethrough, wherein said aperture includes two spaced-apart staple apertures separated by a wall.

14. The surgical apparatus of claim 13, incorporating by reference all of the elements of that claim; further comprising a rail connected to one said protrusion in each said individual insert, whereby said feeder rail is slidable along an upper surface of said rail.

15. The surgical apparatus of claim 14, incorporating by reference all of the elements of that claim; wherein said rail is slidable relative to said protrusions.

16. The surgical apparatus of claim 13, incorporating by reference all of the elements of that claim; wherein said protrusion and rail are generally and collectively T-shaped.

17. Surgical apparatus, comprising:
at least one movable feeder belt;
a plurality of staples fixed to said feeder belt; and
a flexible articulation insert having at least one feeder belt passage defined therein, said flexible articulation insert configured to bend through a range of motion;
wherein each said feeder belt extends through a corresponding said feeder belt passage, and wherein each said feeder belt passage is shaped such that the corresponding said feeder belt and staples fixed thereto are slidable along said passage throughout the entire said range of motion of said flexible articulation insert.

* * * * *